United States Patent [19]

Lau et al.

[11] Patent Number: 5,436,010

[45] Date of Patent: Jul. 25, 1995

[54] HAIR PENETRANT AND CARRIER

[75] Inventors: John R. Lau, Howard; W. Blair Geho, Wooster; Darryl H. Woods, Glenmont, all of Ohio

[73] Assignee: SDG Technology, Inc., Wooster, Ohio

[21] Appl. No.: 99,346

[22] Filed: Jul. 30, 1993

[51] Int. Cl.$^6$ ............................................. A61K 9/127
[52] U.S. Cl. ................................. 424/450; 424/70.1; 424/489; 428/402.2
[58] Field of Search ................. 424/70, 71, 450, 489; 428/402.2

[56] References Cited

U.S. PATENT DOCUMENTS

| | | | |
|---|---|---|---|
| 3,957,971 | 5/1976 | Oleniacz | 424/70 |
| 4,217,344 | 8/1980 | Vanlerberghe et al. | 424/60 |
| 4,772,471 | 9/1988 | Vanlerberghe et al. | 424/450 |
| 5,021,200 | 6/1991 | Vanlerberghe et al. | 424/450 X |
| 5,145,604 | 9/1992 | Neumiller | 252/312 |

Primary Examiner—John Kight, III
Assistant Examiner—Shelley A. Dodson
Attorney, Agent, or Firm—Frijouf, Rust & Pyle

[57] ABSTRACT

This invention discloses the phenomenon of penetrating the hair shaft with a hydroxysphere and glycerin carrier system ("HS-GL"), manufactured using materials that are Generally Regarded As Safe ("GRAS"). The penetration of the hair shaft by the HS-GL carrier system provides a means of transporting materials such as hair care agents, moisturizers, coloring agents, therapeutics, hair setting agents, and agents used for hair care cosmetic applications, through the cuticle and the cortex to the medulla region in the center of the hair shaft. The resulting benefits that can be achieved using this HS-GL carrier system alone, are greater hair manageability, greater ease of combing, higher sheen, better hair set, longer-lasting hair curl, and a restoration of softness in dry hair and also in hair which is brittle and damaged by split ends. Penetration of the hair shaft by the HS-GL carrier system is also reversible with water.

3 Claims, 3 Drawing Sheets

Hydroxysphere (composed of hydroxylated lecithin)
Where:   o = a hydrophilic head group
         = = a pair of hydrophobic acyl chains originally unsaturated which have been hydroxylated
       ... = a hydrogen bond
         G =
$$H-\underset{\underset{H}{|}}{\overset{\overset{OH}{|}}{C}} - \underset{\underset{OH}{|}}{\overset{\overset{H}{|}}{C}} - \underset{\underset{H}{|}}{\overset{\overset{OH}{|}}{C}} - H$$
Glycerol
(trihydroxypropane)

A = Pitch of small helix in alpha-keratin

B = Pitch of large helix in alpha-keratin

C = 7-stranded cable of alpha-keratin

Hydroxysphere (composed of hydroxylated lecithin)

Where:
- o = a hydrophilic head group
- ═ = a pair of hydrophobic acyl chains originally unsaturated which have been hydroxylated
- ... = a hydrogen bond
- G =

Glycerol (trihydroxypropane)

HAIR PENETRANT AND CARRIER

BACKGROUND OF THE INVENTION

Field of the Invention

Hair care products morphology.

From a morphological point of the view the hair shaft consists of elongated keratinizing cells which are cemented together and known collectively as the "cortex."

The cortex is surrounded by an external cuticle which arises from a single line of cells in the bulb of the hair shaft. Eventually the cuticle evolves into five to ten overlapping layers forming an external barrier. When viewed externally, the cuticle scales appear imbricated, similar to the placement of roof tiles, with free edges directed outwardly, thus forming a barrier preventing the free passage of hair care agents.

Hair is composed of an insoluble protein material called keratin, which is formed as the ultimate product of the keratinization process which occurs in the hair follicle. In addition, small quantities of water soluble substances such as pentose sugars, phenols, uric acid, glycogen and glutamic acid, are also present.

As a result of chemical bonding, hair assumes a crosslinked structure depicted as submicroscopic fibrils containing both parallel and linked polypeptide chains. The fibrils are relatively impervious to penetration by outside agents especially in the crystalline regions and is known as the alpha-keratin structure with a helical arrangement. Although this crystalline structure shows a pronounced degree of regularity, it is not to be regarded as crystalline in the sense that it is associated with inorganic materials. Furthermore, it has been determined that the helical structure possesses a more refined internal structure that is also helical in nature. Therefore, there is a helix within a helix. The more closely packed regions of protofibrils contain structures in which six of these screw-shaped helices have twisted about another so as to form a compound helix. This structure resembles a seven-stranded cable as shown in FIG. 1. The cable-like structure is representative of the crystalline regions of alpha keratin.

In addition, these amorphous regions are not protected from outside attack by the structural side chains of the compound helix. However, these amorphous regions do offer a partial barrier allowing the passage of some materials but not others.

Hair has very many characteristics differing from person to person. One of the very common characteristics is dry, brittle hair shafts which break off easily and leave an uneven and unattractive hair appearance. There are many products available on the open market for coating hair to form a softer appearance with a pleasant sheen. However, such products do not possess the carrier potential that is found in the HS-GL carrier system.

It is an object of this invention to penetrate both the crystalline and amorphous hair structure with a character modification chemical.

Specifically, it is an object of this invention to enable a liposome coated with a modified lecithin such as glycerine to penetrate the hair shaft and induce improved character of the hair shaft.

It is a further object of this invention to penetrate the cuticle sheath of a hair structure by a carrier that will transport a humectant into the interior structure of hair to lubricate and humidify the structure of the hair helix.

A still further object of this invention is to provide a modified form of lecithin that will penetrate the fibrils of a hair shaft with a surface modification of glycerin which facilitates penetration of the hair shaft with glycerin and other humectants.

Also, it is an object of this invention to provide improved means for inducing a desired color to hair shafts.

Furthermore it is an object of this invention to provide a modified form of lecithin that will act as a carrier for therapeutic and cosmetic agents.

SUMMARY OF THE INVENTION

Microfluidization of hydroxylated lecithin will produce structures referred to as hydroxyspheres ("HS").

It is a discovery of this invention that the crystalline and amorphous regions of hair can be made penetrable by using a combination of formulated hydroxyspheres together with glycerin ("HS-GL").

Liposomes made from hydroxylated lecithin have been extensively tested by Applicant, and the product is excellent.

From a long experience with hydroxylated lecithin, hydrogenated lecithin, distearoyl lecithin, dipalmitoyl lecithin, dilauroyl lecithin, acetylated lecithin, sulfonated lecithin, Applicant is able to predict with reasonable certainty that many other lipids having the lubricating capacity of glycerin will be useful in producing a delivery system for hair. Collectively these film-forming materials may be included in the expression "HS".

There is one prior patent that is useful to clarify the thrust of the present invention. That patent is Oleniacz U.S. Pat. No. 3,957,971.

Oleniacz is concerned with treating the surface of mammalian skin with liposomes filled with glycerin and humectant.

Penetration to the medulla of a hair shaft is not the concern of this prior art patent. See column 3, lines 45-49. The prior art teaching is to remove the humectant from the surface of the liposome. This invention is the exact opposite. According to this invention, any product may be transported into the hair shaft. Fluorescing agent D10 has been used in the study of this invention, and imparts a yellow-green hue to the hair. Other chemical coloring matter can be carried into the hair, and freely shampooed out if not wanted. This is a unique characteristic of the present invention.

The resultant product of microfluidization forms hydroxyspheres, and when mixed with a polyhydric alcohol, forms a mixture of organic materials with a composition that is generally regarded as safe ("GRAS"). This new HS-GL carrier system is unique and superior to known hair care products. Therefore, to further summarize, the prior art has employed glycerin and similar products in an effort to condition dry hair and produce sheen and good set to the hair. However, there is very little useful advantage to this prior art effort.

The preferred embodiment of the present invention employs hydroxyspheres made from lecithin and the polyhydric alcohol glycerin.

The unique feature characterizing this invention from the prior art is a quick and thorough penetration of hair shaft by the composition of the HS-GL carrier system. This difference from the prior art is outstanding and has been enthusiastically accepted by those who have tested the products in laboratory conditions and in testing on human volunteers.

DETAILED DESCRIPTION

Figure 1:
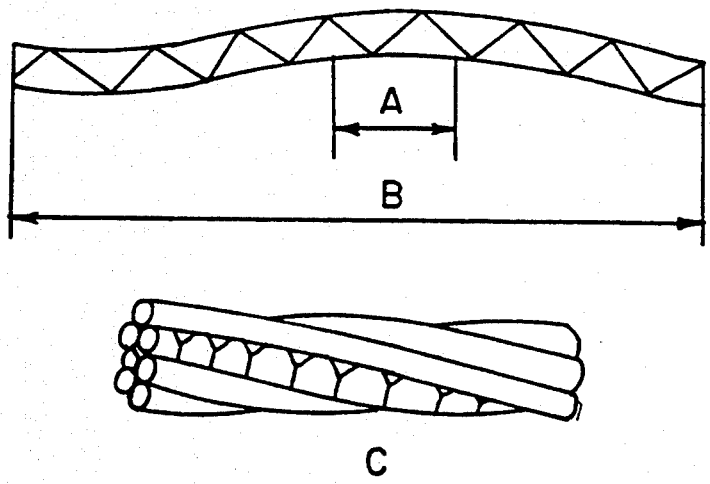
FIG. 1 is a representation of a portion of a hair strand showing hair fibers in a helical entwined relationship, with one of those strands being itself a helix, thereby forming a helix within a helix; and developing into a seven-stranded cable.
Figure 2:
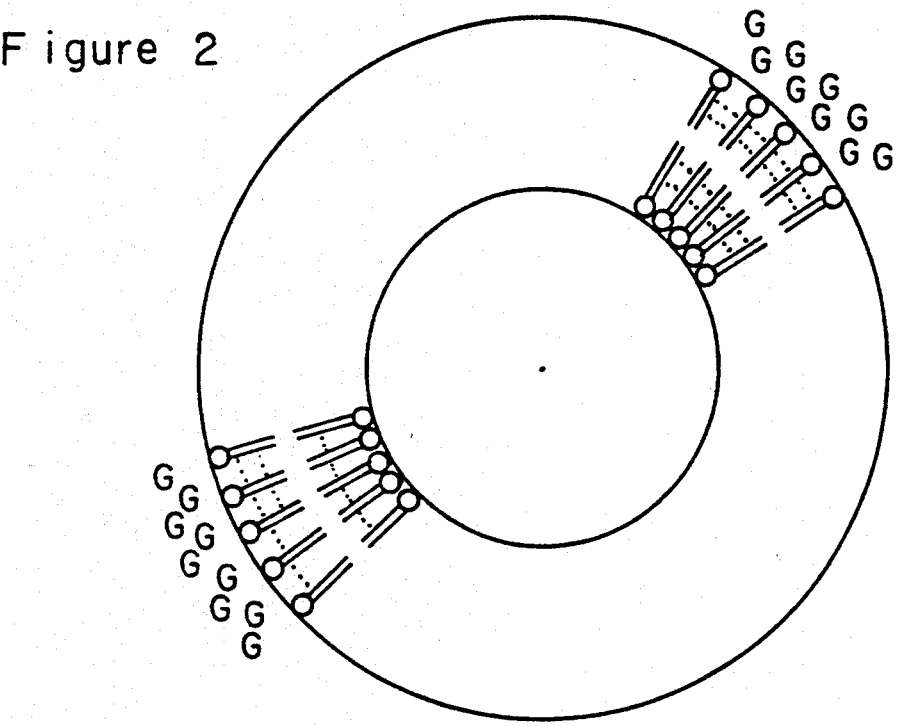
FIG. 2 is a symbolic illustration of a hydroxysphere showing the arrangement of hydrophilic head groups and hydrophobic acyl chain tail groups which form a lipid film. The illustration of that in FIG. 2 is that of a lipid film after being formed into a hydroxysphere. The illustration indicates a series of glycerine molecules attracted to the hydroxysphere surface.
Figure 2:
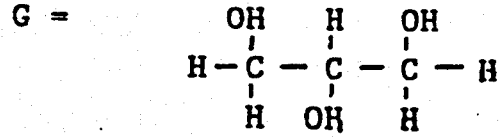

It has been discovered according to this invention that the HS-GL product as described achieves complete penetration as a carrier system to the level of the spiral cell in the functional protofibril and is able to migrate to the central medulla region in the cortex of the hair shaft in the morphological model. The penetration of the hair shaft by the combination of microfluidized hydroxylated lecithin and glycerin according to this invention is unique because penetration is minimal or incomplete when either hydroxylated lecithin, even though microfluidized to hydroxysphere form, or glycerin are treated separately as individual penetrating agents.

There is much more detail in the full study of hair shafts, but sufficient for this application is the observation that glycerine, if transported into the hair shaft, will be a humectant that continues humidifying and moisturizing the hair for an indefinite period of time after application. This goal has not been achieved prior to this invention.

The structure of hair is composed of polypeptide chains which have assumed a helical form wherein each turn of the helix is located relative to the next by hydrogen bond formation.

It is the discovery of this invention that the crystalline and amorphous regions of hair created by the appropriate linking of successive amino acids can be made penetrable by using a combination of hydroxyspheres, together with transported glycerin.

HS, when mixed with the polyhydric alcohol glycerin, forms a mixture of organic materials which is a generally regarded safe composition that is unique and superior to other hair care products because it penetrates the hair shaft as an intact carrier system termed HS-GL. The analytical evaluation of the penetration phenomena has been observed through the use of the fluorescing agent 3,3'-dioctadecyloxacarbocyanine perchlorate ("DiO"). DiO was included as fluorescent marker with all of the agents tested. However, when DiO was evaluated alone for its penetrating capability on the human hair shaft only minimal surface attachment was noted. DiO washed off of the hair shaft easily with distilled water.

Analytical data have indicated that human hair contains a number of acidic side chains contributed by glutamic and aspartic acid amino acid residues and that the number of acidic side chains is approximately double the number of basic side chains contributed by arginine, histidine and lysine. These structural characteristics explain why the isoelectric point of solubilized human hair resides in the range from pH 4.1–4.7 and why a high concentration of positively charged ions will convert all the surplus acidic side chains into the corresponding salts.

In the subsequent ionic exchanges, polyvalent ions will replace monovalent ions (i.e., $Ca^{+2}$ will replace $Na^+$ and $Al^{+3}$ will replace $Ca^{+2}$). Eventually, cations with pronounced surface activity will replace the simple inorganic ions in association with the acidic side chains. This last effect accounts for the fact that cationic detergents are readily absorbed by the hair surface and provides an explanation for why the cationic fluorescer, DiO, has affinity for hair. DiO interacts with the acidic side chains aspartic and glutamic acid and neutralizes their charges, but only at the surface of the hair shaft, as it lacks penetrating capability.

Figure 3:
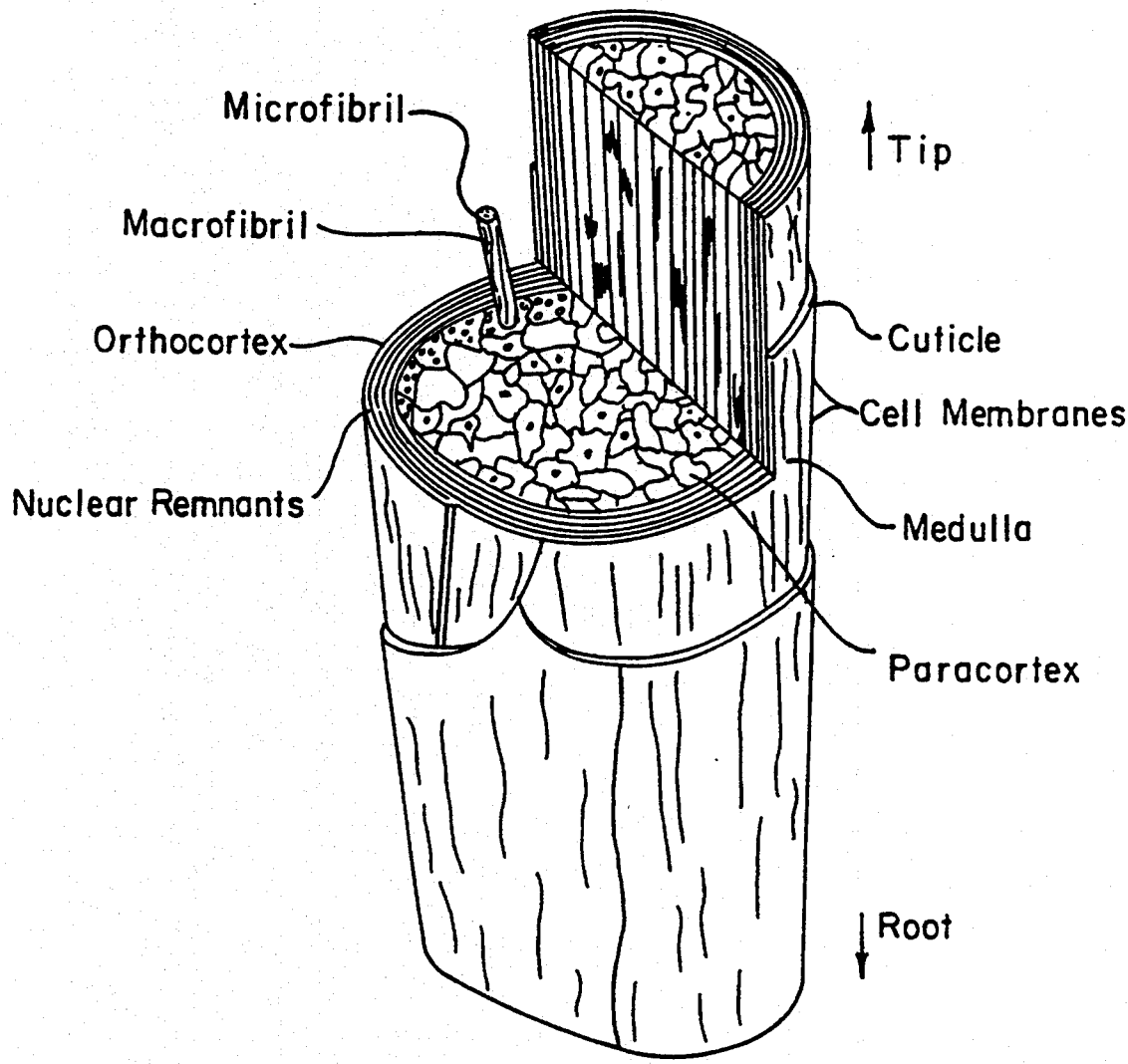
FIG. 3 is a perspective view of a hair shaft illustrating the microfibril, macrofibril, the cuticle, and medulla.

FIG. 3 depicts the hydroxysphere structure prepared using hydroxylated lecithin. Also shown in the figure is a structure of glycerol. Glycerol is depicted interacting with the surface of the hydroxysphere. It is noted that there is a complex of hydroxyl groups that arise from hydroxylated lecithin which provide a network of hydrogen bonds between intra and inter acyl lecithin chains which stabilize the hydroxysphere.

Glycerol functions at a molecular level in this composition by lowering the surface tension of the hydroxysphere membrane which in turn effectively lowers the viscosity of the HS-GL carrier system thereby allowing more effective penetration to the functional units of hair. The penetration phenomena was discovered accidentally and is described as the sequential migration of the HS-GL carrier system through successive alpha keratin polypeptide chains in human hair. In addition to reducing surface tension and lowering viscosity, the glycerol moiety hydrogen bonds to the hydrophilic head group of hydroxylated lecithin and thereby facilitates the bonding of water to the hydrophilic surface.

An exceptional hydrophilic environment on the hydroxysphere surface side in penetrating the hair shaft. This phenomenon is accompaniment with the fact that there is cancellation of charge on the choline portion of this molecule due to ion pair interaction between the negatively charged phosphate functional group and the positively charged terminal quaternary amine group. Collectively, their chemical interaction creates an exceptionally neutral surface. This enables the hydroxysphere to migrate between proteinaceous alpha keratin fibrils to the medulla region of the hair shaft. This migration is due to the lack of ionic and hydrophobic interaction between the surface of the hydroxysphere and the various side chains of the amino acid residues.

While the hair shaft per se is not soluble in aqueous media at neutral pH, the individual helical protein chains are very soluble when isolated individually. This invention exploits the chemical nature of the helical peptide chain and specifically the amino acid side chains in conjunction with the chemistry of the neutral (hydrophilic) surface to create a unique hydroxysphere carrier system that can effectively penetrate to the medulla region of the hair shaft. The resulting benefits that can be observed from the penetration of the hair shaft by (HS-GL) are greater manageability, greater ease of combing, higher sheen, better hair set, and longer-lasting hair curl. The most noticeable effect on hair is the immediate long term restoration of softness in hair that was previously dry and bordered on being brittle and damaged by tangles and split ends. This effect was noted following the initial application of the HS-GL carrier system. In addition, the carrier system eliminates the static electricity effect noticed with the use of most hair care products.

Upon washing hair, water penetrates the hair shaft but is quickly lost with drying. As a result, the hair lacks a good set. Moderate set of hair may be obtained using the HS-GL carrier system. An added benefit of this invention is that the effects of using the HS-GL carrier system can be made reversible by shampooing. In this manner, the HS-GL system can be simply removed from the hair shaft by shampooing without imparting any damaging or deleterious effects. Alternatively, over time, after an HS-GL carrier system application, the hair naturally returns to its condition prior to setting. Such reversibility is in concert with the chemistry of the carrier system, which has a high affinity for aqueous media.

While the HS-GL carrier system forms intra- and inter- hydrogen bonds to facilitate the stability of the hair care product, the hydroxyl groups on the lipid acyl chains also serve another function. If the integrity of the carrier system is ever compromised and there is dissolution of the hydroxysphere structure, the fact that the acyl chains are hydroxylated and more wetable by an aqueous phase, allows them to be removed more readily from an aqueous or hydrophilic environment. As a result the constituents of the (HS-GL) carrier system can be more readily rinsed from the interior of the hair shaft. This property is particularly useful in regards to the safety profile of a new hair care product, which enables it to be removed quickly from a consumer's hair if unwanted effects are noted.

Procedure for the preparation of the hair care product for fluorescent testing of penetration in a human hair shaft.

A 20 percent w/w suspension of hydroxylated lecithin was prepared by suspending 10 g of hydroxylated lecithin in 40 g of distilled water. This suspension was then microfluidized. The resulting hydroxysphere mixture was coded "HS stock A." To 50 g of HS stock A was added HS stock B with mixing. Stock B was prepared by mixing 2.5 g of U.S.P. glycerin and 47.5 g of distilled water. The final combined HS stocks A and B formed the hydroxysphere carrier designated as the HS-GL composition:

| Hydroxylated Lecithin | 10 g | 10% w/w |
|---|---|---|
| Glycerin | 2.5 g | 2.5% w/w |
| Distilled Water | 87.5 g | 87.5% w/w |
| | 100 g | 100% w/w |

2.0 grams of HS-GL was mixed with 2.0 mg of 3,3-dioctadecyloxacarbocyanine perchlorate to formulate the hair penetrating agent. This mixture was sonicated in a polycarbonate tube using a Teckmar sonic disrupter equipped with a water-jacketed cup horn at power setting #4 for 3.0 minutes. The temperature during sonication rose from an ambient temperature to +70 degree C. The final color was yellowish opalescent. The resultant HS-GL carrier system was evaluated for its hair penetrating ability using hairs dipped in HS-GL. The average particle size in this preparation was 100 nm.

The materials used for the formulation procedures are as follows:

1) Commercially available hydroxylated lecithin;
2) Commercially available glycerin, U.S.P. No. 99.9%

EXAMPLE 2: In setting up a test to determine the actual function of the described combination brought about a surprising discovery of yet a second useful purpose for this invention.

The analytical evaluation of the penetration phenomena has been observed through the use of fluorescing agent 3,3-dioctadecyloxacarbocyanine perchlorate ("DiO"). DiO was introduced as a fluorescent marker with all the agents tested. Thus, with DiO as a marker, it was established conclusively that the HS-GL carrier system actually penetrates the cuticle surrounding the hair shaft and enters the cortex.

When DiO is used as a marker, it produces a yellowish-green color to the hair. That effect is quite sufficient for testing and proving concepts, but also leads to the discovery herein that other coloring matter, like DiO, may be devised to enter the hair shaft by this same means and therefore produce different shades and colors of hair. Accordingly, the second useful purpose for this same product has been determined.

It is noted that when DiO was evaluated alone for its penetrating ability on the human hair shaft, only minimal surface attachment was noted. DiO washed off the hair shaft easily with distilled water.

The conclusion is that the use of HS-GL may carry products into the hair shaft which normally would not be capable of entering therein, and it may be used for softening the hair or coloring the hair. Although not tested or studied in depth, it is also within the realm of this invention to provide antibiotics or other therapeutic agents through the hair by means of this HS-GL carrier system.

What is claimed is:

1. A therapeutic and cosmetic delivery system for treating hair, comprising hydroxyspheres, said hydroxyspheres consisting of lecithin lubricant selected from the class consisting of hydroxylated lecithin, hydrogenated lecithin, distearoyl lecithin, dipalmitoyl lecithin, dilauroyl lecithin, acetylated lecithin, sulfonated lecithin in combination with glycerin, said glycerin coats only the surface of the hydroxyspheres, said combination of lecithin and glycerin facilitating penetration of the hydroxysphere throughout a hair shaft.

2. A delivery system for transport of a material into the cortex of hair comprising, a modified lecithin in hydroxysphere form with a hydrophilic external surface, and at least one glycerin attached to and carried by said hydroxysphere surfaces.

3. A combination comprising:
an amphipathic phospholipid selected from the class consisting of a modified lecithin, developed into hydroxyspheres; said hydroxyspheres modified by molecules selected from the class consisting of propylene glycol, sorbitol, ethylene glycol and polypropylene glycol;
whereby said combination will penetrate a hair shaft to place the agent to be delivered into the hair; and
whereby said penetration may be reversed by means of rinsing the hair with water.

* * * * *